United States Patent
Barere et al.

(10) Patent No.: US 10,842,612 B2
(45) Date of Patent: Nov. 24, 2020

(54) BREAST TREATMENT DEVICE

(71) Applicant: LifeCell Corporation, Branchburg, NJ (US)

(72) Inventors: Aaron M. Barere, Hoboken, NJ (US); Sangwook Park, Dunellen, NJ (US); Evan J. Friedman, Montvale, NJ (US); Kai-Roy Wang, Jersey City, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

(21) Appl. No.: 15/241,388

(22) Filed: Aug. 19, 2016

(65) Prior Publication Data

US 2017/0071725 A1 Mar. 16, 2017

Related U.S. Application Data

(60) Provisional application No. 62/208,366, filed on Aug. 21, 2015.

(51) Int. Cl.
*A61F 2/12* (2006.01)
*A61L 27/36* (2006.01)

(52) U.S. Cl.
CPC .............. *A61F 2/12* (2013.01); *A61L 27/362* (2013.01); *A61L 27/3633* (2013.01); *A61L 27/3695* (2013.01); *A61F 2230/0013* (2013.01)

(58) Field of Classification Search
CPC ........... A61F 2/12; A61F 2/0063; A61B 90/02
See application file for complete search history.

(56) References Cited

U.S. PATENT DOCUMENTS

| | | | |
|---|---|---|---|
| 954,767 A | 4/1910 | Saunders | |
| 997,575 A | 7/1911 | Mitchell | |
| 2,108,205 A | 2/1938 | Martin | |
| 2,671,444 A * | 3/1954 | Pease, Jr. | ............. A61F 2/0063 606/151 |
| 3,683,424 A | 8/1972 | Pangman | |
| 4,298,998 A | 11/1981 | Naticy | |
| 4,573,999 A * | 3/1986 | Netto | ........................ A61F 2/12 623/7 |
| 4,840,629 A | 6/1989 | Bustos | |
| 4,936,858 A | 6/1990 | O'Keeffe | |
| 4,984,585 A | 1/1991 | Austad | |
| 5,352,307 A | 10/1994 | Wild | |

(Continued)

FOREIGN PATENT DOCUMENTS

CN 1953657 A 4/2007
DE 102006029605 A1 12/2007
(Continued)

OTHER PUBLICATIONS

International Search Report and Written Opinion of corresponding application PCT/US2016/047713, dated Nov. 22, 2016.
(Continued)

*Primary Examiner* — Seema Mathew (57) ABSTRACT

The present disclosure provides devices and methods for treating the breast. The devices can include an acellular tissue matrix having a predefined shape. The shape can include a first edge with an S-shaped configuration and a second arcuate-shaped edge. The shape alternatively can include a first concave edge and a second convex edge.

30 Claims, 7 Drawing Sheets

(56) References Cited

U.S. PATENT DOCUMENTS

| | | | |
|---|---|---|---|
| 5,356,429 A * | 10/1994 | Seare | A61F 2/12 623/8 |
| 5,447,535 A | 9/1995 | Muller | |
| 5,584,884 A | 12/1996 | Pignataro | |
| 5,658,328 A | 8/1997 | Johnson et al. | |
| 5,658,330 A | 8/1997 | Carlisle et al. | |
| 5,676,161 A * | 10/1997 | Breiner | A61B 17/32053 128/898 |
| 5,713,959 A | 2/1998 | Bartlett et al. | |
| 5,733,337 A | 3/1998 | Carr, Jr. et al. | |
| 5,755,791 A | 5/1998 | Whitson et al. | |
| 5,954,767 A | 9/1999 | Pajotin et al. | |
| 5,968,096 A | 10/1999 | Whitson et al. | |
| 5,997,575 A | 12/1999 | Whitson et al. | |
| 6,066,777 A * | 5/2000 | Benchetrit | A61F 2/0063 424/423 |
| 6,099,566 A | 8/2000 | Vonderharr et al. | |
| 6,203,570 B1 | 3/2001 | Baeke | |
| 6,210,439 B1 | 4/2001 | Firmin et al. | |
| 6,334,868 B1 | 1/2002 | Ham | |
| 6,368,541 B1 | 4/2002 | Pajotin et al. | |
| 6,464,726 B1 * | 10/2002 | Heljenek | A61F 2/12 623/8 |
| 6,638,308 B2 | 10/2003 | Corbitt, Jr. et al. | |
| 6,666,892 B2 | 12/2003 | Hiles et al. | |
| 6,723,133 B1 * | 4/2004 | Pajotin | A61F 2/0063 606/151 |
| 6,736,823 B2 | 5/2004 | Darois et al. | |
| 6,736,854 B2 | 5/2004 | Vadurro et al. | |
| 6,740,122 B1 * | 5/2004 | Pajotin | A61F 2/0063 606/151 |
| 6,777,231 B1 | 8/2004 | Katz et al. | |
| 6,802,861 B1 | 10/2004 | Hamas | |
| 7,011,688 B2 | 3/2006 | Gryska et al. | |
| 7,081,135 B2 | 7/2006 | Smith et al. | |
| 7,358,284 B2 | 4/2008 | Griffey et al. | |
| 7,470,537 B2 | 12/2008 | Hedrick et al. | |
| 7,476,249 B2 * | 1/2009 | Frank | A61F 2/12 623/8 |
| 7,658,727 B1 | 2/2010 | Fernandes et al. | |
| 7,699,895 B2 | 4/2010 | Hiles et al. | |
| 7,875,074 B2 | 1/2011 | Chen et al. | |
| 8,007,531 B2 * | 8/2011 | Frank | A61F 2/12 623/8 |
| 8,128,708 B2 | 3/2012 | Hiles et al. | |
| 8,192,486 B2 | 6/2012 | Glicksman | |
| 8,313,527 B2 | 11/2012 | Powell et al. | |
| 8,383,092 B2 | 2/2013 | Lee et al. | |
| 8,487,012 B2 | 7/2013 | Goraltchouk et al. | |
| 8,685,296 B2 | 4/2014 | Liu et al. | |
| 8,858,647 B2 | 10/2014 | Markman | |
| 8,876,899 B2 * | 11/2014 | Maxwell | A61F 2/12 623/8 |
| 8,961,617 B2 * | 2/2015 | Young | A61F 2/02 623/23.72 |
| 8,986,377 B2 * | 3/2015 | Richter | A61L 27/3695 623/8 |
| 9,011,550 B2 * | 4/2015 | Soares Da Costa | A61F 2/0063 623/23.72 |
| 9,486,200 B2 * | 11/2016 | Melsheimer | A61B 17/0281 |
| 9,549,812 B2 | 1/2017 | Shetty et al. | |
| 9,603,698 B2 * | 3/2017 | Kerr | A61F 2/12 |
| 9,713,519 B2 * | 7/2017 | Horton | A61L 31/022 |
| 9,867,686 B2 * | 1/2018 | Soares Da Costa | A61F 2/0063 |
| 9,901,440 B2 * | 2/2018 | Liu | A61L 27/3641 |
| 10,004,590 B2 | 6/2018 | Shetty | |
| 10,335,257 B2 * | 7/2019 | Rizk | A61F 2/0063 |
| 10,449,034 B2 | 10/2019 | Bowley et al. | |
| 10,675,137 B2 * | 6/2020 | Bailly | A61F 2/0063 |
| 2001/0041936 A1 | 11/2001 | Corbitt et al. | |
| 2002/0103542 A1 | 8/2002 | Bilbo | |
| 2003/0036803 A1 | 2/2003 | McGhan | |
| 2003/0130747 A1 | 7/2003 | Abraham et al. | |
| 2003/0212461 A1 | 11/2003 | Vadurro et al. | |
| 2003/0212462 A1 | 11/2003 | Gryska et al. | |
| 2003/0225355 A1 | 12/2003 | Butler | |
| 2004/0049269 A1 | 3/2004 | Corbitt et al. | |
| 2004/0260315 A1 | 12/2004 | Dell et al. | |
| 2005/0021141 A1 | 1/2005 | Bleyer et al. | |
| 2005/0119737 A1 | 6/2005 | Bene et al. | |
| 2005/0165425 A1 | 7/2005 | Croce et al. | |
| 2005/0187624 A1 | 8/2005 | Corbitt | |
| 2005/0250977 A1 | 11/2005 | Montpetit et al. | |
| 2005/0260176 A1 | 11/2005 | Ayares et al. | |
| 2006/0030939 A1 | 2/2006 | Frank | |
| 2006/0064175 A1 * | 3/2006 | Pelissier | A61F 2/0063 623/23.72 |
| 2006/0167338 A1 * | 7/2006 | Shfaram | A61B 17/0401 600/37 |
| 2006/0206189 A1 | 9/2006 | Furst et al. | |
| 2007/0038299 A1 | 2/2007 | Stone et al. | |
| 2007/0088299 A1 | 4/2007 | Ayre | |
| 2007/0088434 A1 | 4/2007 | Frank | |
| 2007/0116678 A1 | 5/2007 | Sung et al. | |
| 2007/0250177 A1 | 10/2007 | Bilbo | |
| 2007/0276487 A1 * | 11/2007 | Carteron | A61F 2/0063 623/11.11 |
| 2008/0027273 A1 * | 1/2008 | Gutterman | A61B 17/84 600/37 |
| 2008/0027542 A1 | 1/2008 | McQuillan et al. | |
| 2008/0082113 A1 | 4/2008 | Bishop et al. | |
| 2008/0097601 A1 * | 4/2008 | Codori-Hurff | A61F 2/12 623/8 |
| 2008/0108134 A1 | 5/2008 | Murphy et al. | |
| 2008/0167729 A1 | 7/2008 | Nelson et al. | |
| 2008/0241212 A1 | 10/2008 | Moses et al. | |
| 2008/0260853 A1 | 10/2008 | Firestone | |
| 2008/0281418 A1 | 11/2008 | Firestone | |
| 2008/0281419 A1 | 11/2008 | Matheny et al. | |
| 2009/0024227 A1 | 1/2009 | Lesh | |
| 2009/0024228 A1 | 1/2009 | Lesh | |
| 2009/0082864 A1 * | 3/2009 | Chen | A61F 2/12 623/8 |
| 2009/0125107 A1 * | 5/2009 | Maxwell | A61L 27/362 623/8 |
| 2009/0198332 A1 | 8/2009 | Becker | |
| 2009/0216338 A1 | 8/2009 | Gingras et al. | |
| 2009/0240342 A1 | 9/2009 | Lindh, Sr. et al. | |
| 2009/0255618 A1 * | 10/2009 | Tassone | A61F 2/12 156/61 |
| 2010/0010627 A1 | 1/2010 | Matheny | |
| 2010/0023029 A1 * | 1/2010 | Young | A61F 2/0063 606/151 |
| 2010/0028396 A1 | 2/2010 | Ward et al. | |
| 2010/0191330 A1 | 7/2010 | Lauryssen et al. | |
| 2010/0204791 A1 * | 8/2010 | Shfaram | A61B 17/0401 623/8 |
| 2010/0217388 A1 | 8/2010 | Cohen et al. | |
| 2010/0226960 A1 | 9/2010 | Chudzik et al. | |
| 2010/0303880 A1 | 12/2010 | Reddy et al. | |
| 2010/0303886 A1 | 12/2010 | Janis | |
| 2011/0009960 A1 * | 1/2011 | Altman | A61F 2/0059 623/8 |
| 2011/0022171 A1 * | 1/2011 | Richter | A61L 27/3695 623/8 |
| 2011/0035004 A1 | 2/2011 | Maxwell | |
| 2011/0082481 A1 | 4/2011 | Gingras et al. | |
| 2011/0151011 A1 | 6/2011 | Flynn | |
| 2011/0177150 A1 | 7/2011 | Pathak et al. | |
| 2011/0257761 A1 * | 10/2011 | Mortarino | A61F 2/0063 623/23.72 |
| 2011/0276039 A1 | 11/2011 | Markman | |
| 2011/0293666 A1 | 12/2011 | Wang et al. | |
| 2011/0293667 A1 | 12/2011 | Baksh et al. | |
| 2012/0052040 A1 | 3/2012 | Hunter et al. | |
| 2012/0158134 A1 | 6/2012 | Codori-Hurff et al. | |
| 2012/0255047 A1 | 10/2012 | Phelps et al. | |
| 2012/0283826 A1 * | 11/2012 | Moses | A61F 2/0063 623/8 |
| 2013/0053956 A1 | 2/2013 | Powell et al. | |
| 2013/0085579 A1 | 4/2013 | Markman | |
| 2013/0224260 A1 | 8/2013 | Ward et al. | |

(56) References Cited

U.S. PATENT DOCUMENTS

| | | | |
|---|---|---|---|
| 2013/0238100 A1* | 9/2013 | Young | A61F 2/02 623/23.72 |
| 2013/0253645 A1* | 9/2013 | Kerr | A61F 2/0063 623/8 |
| 2013/0273145 A1 | 10/2013 | Vail | |
| 2013/0296897 A1* | 11/2013 | Trupiano | A61F 2/0077 606/151 |
| 2014/0039617 A1 | 2/2014 | Maxwell | |
| 2014/0088700 A1* | 3/2014 | Mortarino | A61L 27/3604 623/8 |
| 2014/0141053 A1 | 5/2014 | Guillemette et al. | |
| 2014/0257481 A1 | 9/2014 | Brooks et al. | |
| 2014/0257482 A1 | 9/2014 | Ward et al. | |
| 2014/0276993 A1 | 9/2014 | Reilly et al. | |
| 2014/0379007 A1* | 12/2014 | Soares Da Costa | A61F 2/0063 606/151 |
| 2015/0012089 A1* | 1/2015 | Shetty | A61F 2/0077 623/8 |
| 2015/0088168 A1* | 3/2015 | Hamlin | A61F 2/0063 606/151 |
| 2015/0112434 A1* | 4/2015 | Felix | B29C 47/08 623/8 |
| 2015/0119353 A1 | 4/2015 | Vail | |
| 2015/0150674 A1* | 6/2015 | Ansorge | A61B 90/02 623/8 |
| 2015/0157451 A1 | 6/2015 | Bowley et al. | |
| 2015/0223928 A1* | 8/2015 | Limem | A61F 2/12 623/8 |
| 2015/0250574 A1* | 9/2015 | Egnelov | A61F 2/0063 606/151 |
| 2015/0250582 A1* | 9/2015 | Greenhalgh | A61F 2/12 623/8 |
| 2015/0313708 A1 | 11/2015 | Mayo | |
| 2015/0359622 A1 | 12/2015 | Matheny | |
| 2015/0359933 A1 | 12/2015 | Matheny | |
| 2015/0374830 A1 | 12/2015 | McKay | |
| 2016/0108144 A1 | 4/2016 | Vail | |
| 2016/0199173 A1* | 7/2016 | Liu | A61L 27/3641 623/8 |
| 2016/0228236 A1* | 8/2016 | Egnelov | A61F 2/12 |
| 2016/0256259 A1 | 9/2016 | Wirth et al. | |
| 2016/0324618 A1 | 11/2016 | Greenhalgh et al. | |
| 2016/0331504 A1* | 11/2016 | Wang | A61F 2/0063 |
| 2017/0007394 A1 | 1/2017 | Shetty et al. | |
| 2017/0027678 A1 | 2/2017 | Greenhalgh et al. | |
| 2017/0056157 A1 | 3/2017 | Hayzlett | |
| 2017/0065822 A1 | 3/2017 | Mashiach et al. | |
| 2017/0071725 A1* | 3/2017 | Barere | A61L 27/3633 |
| 2017/0100509 A1 | 4/2017 | Sun et al. | |
| 2017/0143475 A1* | 5/2017 | Moses | A61F 2/12 |
| 2017/0258574 A1* | 9/2017 | Hutmacher | A61F 2/12 |
| 2017/0296186 A1* | 10/2017 | Bengtson | A61B 17/064 |
| 2017/0340437 A1 | 11/2017 | Bowley et al. | |
| 2017/0348088 A1* | 12/2017 | Bunce | A61F 2/105 |
| 2017/0367807 A1* | 12/2017 | Chen | A61L 27/3691 |
| 2018/0055624 A1 | 3/2018 | Barere et al. | |
| 2018/0092737 A1* | 4/2018 | Barere | A61F 2/12 |
| 2018/0228598 A1* | 8/2018 | Mathisen | A61B 90/02 |
| 2019/0117362 A1* | 4/2019 | Daunch | A61L 27/50 |
| 2019/0201580 A1 | 7/2019 | Barere et al. | |
| 2020/0008930 A1 | 1/2020 | Bowley et al. | |

FOREIGN PATENT DOCUMENTS

| | | |
|---|---|---|
| EP | 3034038 A1 | 6/2016 |
| FR | 2682284 A1 | 4/1993 |
| FR | 2746298 A1 | 9/1997 |
| JP | H0947503 A | 2/1997 |
| JP | H10-158906 A | 6/1998 |
| JP | 2005-536228 A | 12/2005 |
| WO | 2004028243 A2 | 4/2004 |
| WO | 2004096098 A1 | 11/2004 |
| WO | 2005089411 A2 | 9/2005 |
| WO | 2006115892 A2 | 11/2006 |
| WO | 2006135998 A2 | 12/2006 |
| WO | 2007004214 A2 | 1/2007 |
| WO | 2007134134 A2 | 11/2007 |
| WO | 2008016919 A2 | 2/2008 |
| WO | 2008121816 A2 | 10/2008 |
| WO | 2009001293 A1 | 12/2008 |
| WO | 2009065013 A1 | 5/2009 |
| WO | 2011011394 A3 | 3/2011 |
| WO | 2012/122215 A2 | 9/2012 |
| WO | 2015/065923 A1 | 5/2015 |
| WO | 2016/186803 A1 | 11/2016 |

OTHER PUBLICATIONS

Musculoskeletal Transplant Foundation, Flex HD.

Musculoskeletal Transplant Foundation, Flex HD Max, 2016.

Musculoskeletal Transplant Foundation, Flex HD Instructions, 2012.

Baxter, R.A., "Intracapsular Allogenic Dermal Grafts for Breast Implant-Related Problems", Plast. Reconstr. Surg., 112(6): 1692-1696 (2003).

Breuing, K.H. et al., "Immediate Bilateral Breast Reconstruction With Implants and Inferolateral AlloDerm Slings", Annals of Plastic Surgery, 55(3): 232-239 (2005).

Breuing, K.H. et al., "Inferolateral AlloDerm Hammock for Implant Coverage in Breast Cadaveric Dermal Slings", Annals of Plastic Surgery, 59(3): 250-255 (2007).

Colwell, A.S. et al., "Improving Shape and Symmetry in Mastopexy With Autologous or Cadaveric Dermal Slings", Annals of Plastic Surgery, 61(2): 138-142 (2008).

Darcy, C.M., "A Technique for Preparing Meshed Skin Grafts With Planned Expansion Ratios", British Journal of Plastic Surgery, 56(1): 77-79 (2003).

Duncan, D.I., "Correction of Implant Rippling Using Allograft Dermis", Aesthetic Surgery Journal, 21 (1): 81-84 (2001).

Gamboa-Bobadilla, G.M., "Implant Breast Reconstruction using Acellular Dermal Matrix", Annals of Plastic Surgery, 56(1): 22-25 (2006).

Salzberg, C.A., "Nonexpansive Immediate Breast Reconstruction using Human Acellular Tissue Matrix Graft (AlloDerm)", Annals of Plastic Surgery, 57(1): 1-5 (2006).

Topol, B.M. et al., "Immediate Single-Stage Breast Reconstruction using Implants and Human Acellular Dermal Tissue Matrix With Adjustment of the Lower Pole of the Breast to Reduce Unwanted Lift", Annals of Plastic Surgery, 61 (5): 194-499 (2008).

Zienowicz, R.J. et al., "Implant-Based Breast Reconstruction With Allograft", Plast. Reconstr. Surg., 120: 373-374 (2007).

Goes, Joao C.S., "Periareolar Mastopexy and Reduction with Mesh Support, Double Skin Technique", Surgery of the Breast: Principles and Art. Scott L Spear (Ed.), Lippincott-Raven Publishers, Philidelphia. Chapter 51, pp. 697-708 (1998).

Goes, Joao C.S., "Periareolar Mastopexy: Double Skin Technique with Mesh Support", Aesthetic Surgery Journal, Mar.-Apr. 2003:23:129-135.

Goes, Joao C.S., "Periareolar Mammaplasty: Double Skin Technique with Application of Polygractine 910 Mesh", Rev. Soc. Bras. Cir. Plast. Estet. Reconstr, 7(1, 2, 3) (1992).

Goes, Joao C.S., "Periareolar Mammaplasty: Double Skin Technique with Application of Polyglactine or Mixed Mesh", Plastic and Reconstructive Surgery (Apr. 1996).

Pope, Eric R., "Mesh Skin Grafting", Veterinary Clinics of North America: Small Animal Practice, vol. 20, No. 1, pp. 177-187 (Jan. 1990).

Goes, Joao C.S., "Periareolar Mammaplasty With Mixed Mesh Support: The Double Skin Technique", Operative Techniques in Plastic and Reconstructive Surgery, vol. 3, No. 3, pp. 199-206 (Aug. 1996).

Goes, Joao C.S. et al., "The Application of Mesh Support in Periareolar Breast Surgery: Clinical and Mammoqraphic Evaluation", Aesth. Plast. Surq., 28:268-274 (2004).

Chinese First Office Action corresponding to CN201510397303.6, dated Sep. 9, 2016.

(56) References Cited

OTHER PUBLICATIONS

Bindingnavele et al., "Use of acellular cadaveric dermis and tissue expansion in postmastectomy breast reconstruction", Journal of Plastic, Reconstructive, and Aesthetic Surgery, 60(2007): 1214-1218.
Non Final Rejection for corresponding U.S. Appl. No. 14/620,667, dated Dec. 28, 2017.
Final Rejection for corresponding U.S. Appl. No. 14/620,667, dated May 29, 2018.
Non-Final Rejection for corresponding U.S. Appl. No. 15/680,666, dated Jun. 22, 2018.

* cited by examiner

BREAST TREATMENT DEVICE

This application claims the benefit, under 35 U.S.C. § 119(e), of the filing of U.S. Provisional Patent Application No. 62/208,366, entitled "Breast Treatment Device," filed Aug. 21, 2015, which is incorporated herein by reference for all purposes.

The present disclosure relates generally to devices for improving breast surgeries, including tissue matrices specially shaped and sized for breast reconstruction or augmentation.

The use of acellular tissue matrices such as ALLODERM®, a dermal acellular matrix produced by LIFECELL® CORPORATION (Branchburg, N.J.)), for use in breast procedures has become increasingly popular with plastic surgeons. Such materials provide a number of advantages and can be used to replace or augment supportive structures after, for example, mastectomy. Such materials can also be useful in aesthetic procedures (e.g., breast augmentation) by providing additional support for breast implants, allowing improved control of breast shape, preventing skin rippling, and/or preventing or treating other problems that may occur with breast augmentation (e.g., symmastia and bottoming out.)

For many surgical procedures, in order to achieve desired results, positioning an implant with respect to anatomical structure and other medical devices is important. To improve both surgical results and efficiency, pre-sized and pre-shaped tissue matrices can be beneficial. The present application provides improved breast treatment devices including tissue matrix materials specially shaped and sized to improve surgical breast procedures.

Accordingly, in some embodiments, a breast treatment device is provided. The device can include a sheet of acellular tissue matrix, wherein the sheet of acellular tissue matrix comprises a flexible sheet with a top surface, a bottom surface, and a peripheral border. In one embodiment, the peripheral border comprises a first edge having a substantially S-shaped configuration, and an arcuate-shaped second edge. In another embodiment, the peripheral border comprises a first edge having a concave shape, and a convex-shaped second edge.

Also provided is a breast treatment system including a breast implant or tissue expander. The system can also include a sheet of acellular tissue matrix, wherein the sheet of acellular tissue matrix comprises a flexible sheet with a top surface, a bottom surface, and a peripheral border. In one embodiment, the peripheral border comprises a first edge having a substantially S-shaped configuration, and an arcuate-shaped second edge. In another embodiment, the peripheral border comprises a first edge having a concave shape, and a convex-shaped second edge.

Also provided are methods of treating a breast. The methods can include identifying an anatomic site within a breast and selecting a breast treatment device comprising a sheet of acellular tissue matrix. The methods can further include implanting the treatment device in or proximate the breast and securing at least a portion of the treatment device to tissue in or near the breast. The sheet of acellular tissue matrix can comprise a flexible sheet with a top surface, a bottom surface, and a peripheral border. In one embodiment, the peripheral border comprises a first edge having a substantially S-shaped configuration, and an arcuate-shaped second edge. In another embodiment, the peripheral border comprises a first edge having a concave shape, and a convex-shaped second edge. The method can include securing at least a portion of the second edge and/or additional parts of the tissue matrix to tissue in or near the breast.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates generally to devices for surgical breast procedures and systems and methods relating to such devices. The devices can be used for tissue augmentation, repair or regeneration of damaged tissue, and/or correction of tissue defects. As such, the devices, systems, and methods discussed herein can be suitable for a wide range of surgical applications, such as, for example, aesthetic surgery, breast reconstruction, breast augmentation, breast enhancement, breast reduction, and revisionary breast surgeries.

Figure 1:
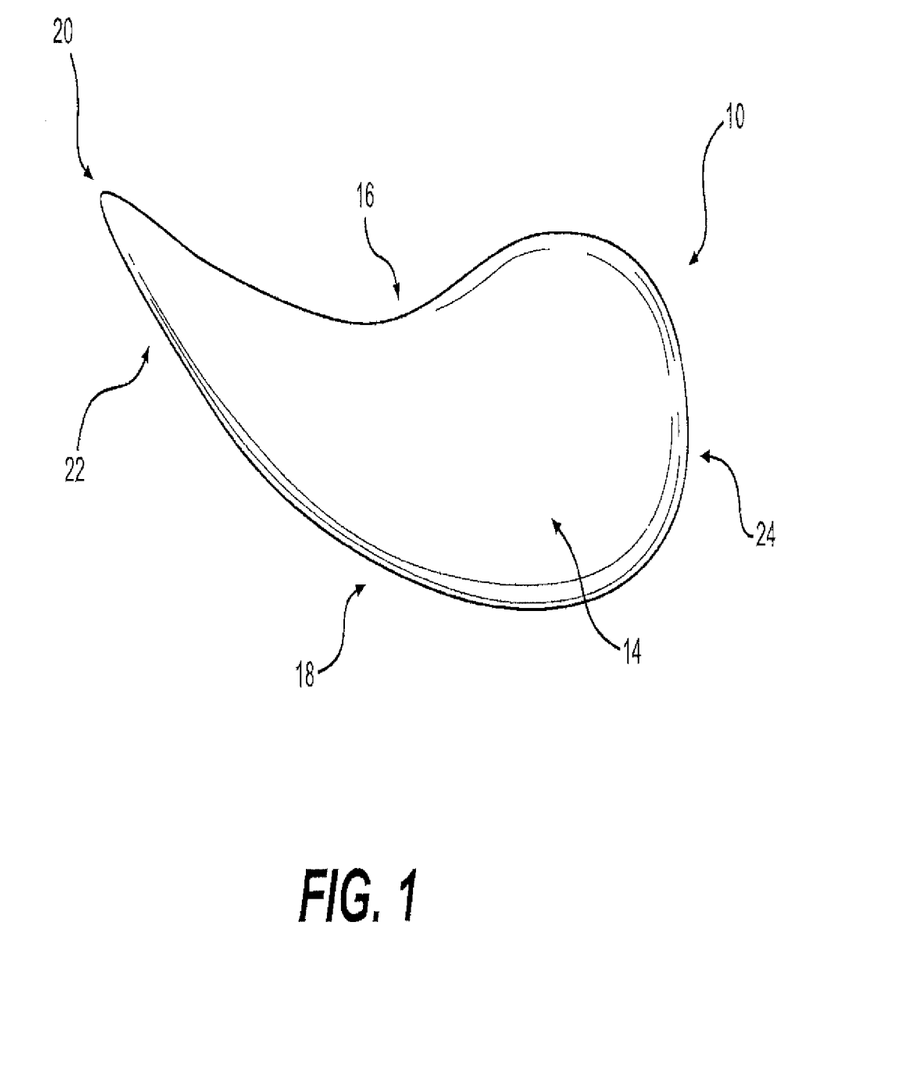
FIG. 1 illustrates a breast treatment device, including a pre-shaped tissue matrix, according to certain embodiments.
Figure 2:
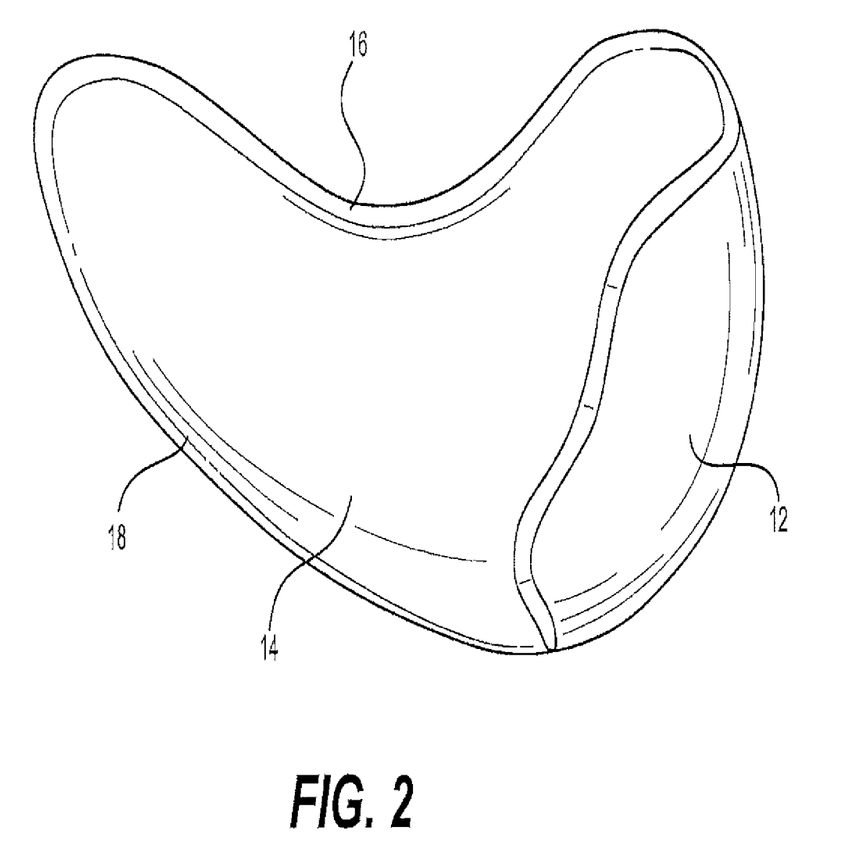
FIG. 2 illustrates a perspective view of a breast treatment device, including a pre-shaped tissue matrix, according to certain embodiments.
Figure 3:
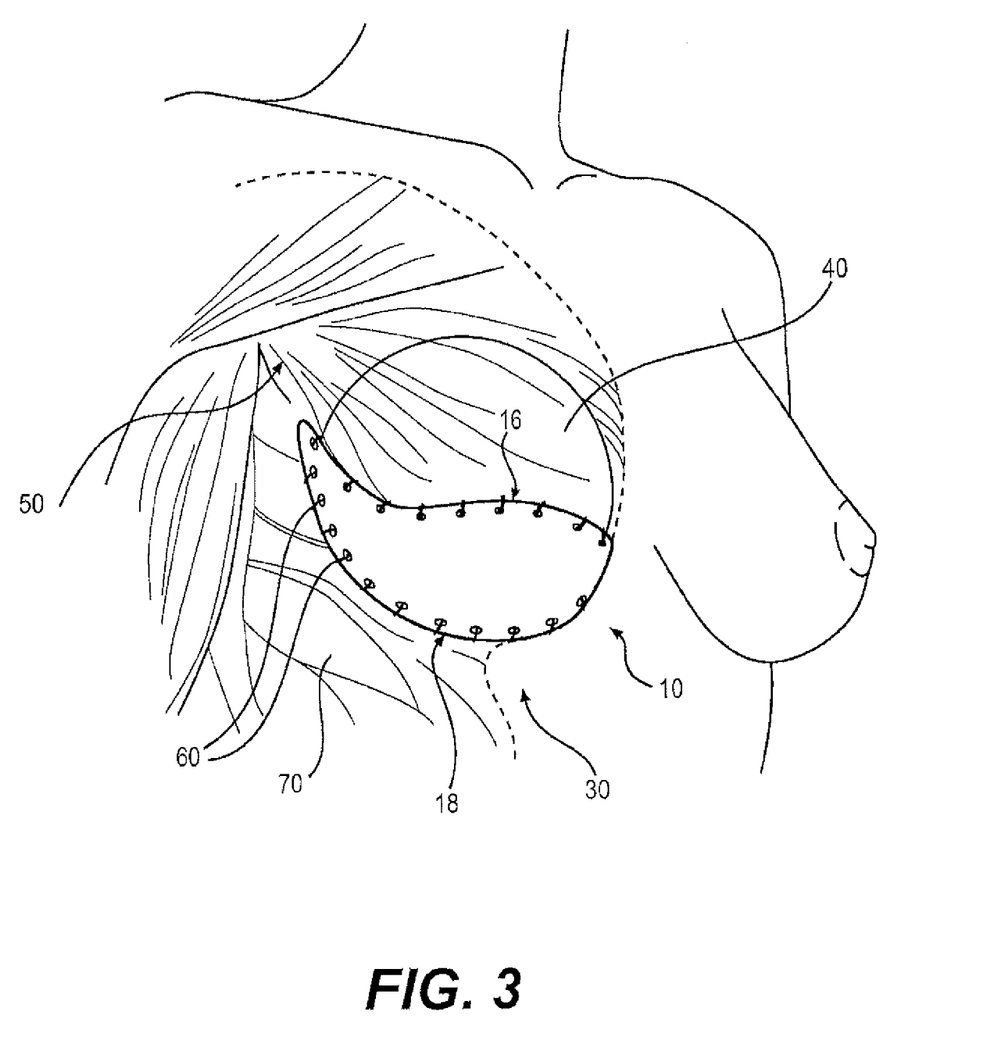
FIG. 3 illustrates implantation of a system for surgical breast procedures, including a pre-shaped tissue matrix implanted along with a breast implant or tissue-expander, according to certain embodiments.

FIG. 1 illustrates a breast treatment device 10, including a pre-shaped tissue matrix, according to certain embodiments, and FIG. 2 illustrates a perspective view of the device 10 of FIG. 1. The device 10 can include a sheet of acellular tissue matrix. The sheet can be a flexible material with a top surface 14, a bottom surface 12 (FIG. 2), and a peripheral border. The peripheral border can include at least two edges 16, 18, including a first edge 16 having a substantially S-shaped configuration, and an arcuate-shaped second edge 18. As discussed below, the device 10 can form part of a treatment system 30, including a breast implant or tissue expander (FIG. 3).

Figure 4:
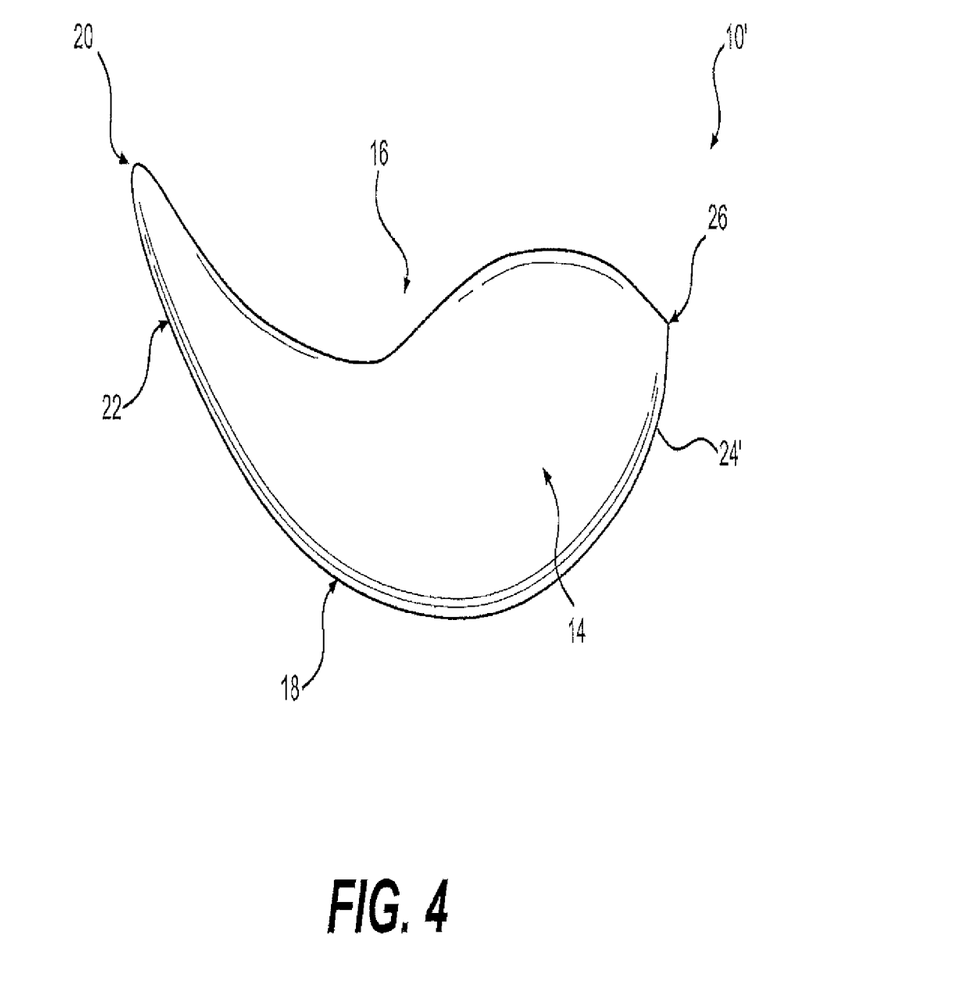
FIG. 4 illustrates a breast treatment device, including a pre-shaped tissue matrix, according to other embodiments.

The first edge 16 and second edge 18 can be joined to one another in a variety of configurations. For example, in one embodiment the first edge 16 and second edge 18 meet at a first end 22 of the device 10 and at a second end 24 of the device 10. Furthermore, the shape of the device at the first end 22 and/or second end 24 can have a variety of configurations, including a pointed tip 20, a rounded shape (FIGS. 1 and 2 at second end 24)), a curvilinear shape, or any other suitable configuration. In one embodiment, both the first end 22 and second end 24 have a pointed tip 20, 26. (FIG. 4).

As noted above, the devices discussed herein can be used for treatment of a breast. Accordingly, the devices 10 can be part of a system 30 for treating a breast—the system 30 including a device 10 and an implant such as a breast implant or breast tissue expander 40. A variety of suitable implants (e.g., saline filled breast implants) and tissue expanders can be used.

The tissue matrices used to produce the devices described herein can include a variety of different materials. For example, an acellular tissue matrix or other tissue product can be selected to allow tissue ingrowth and remodeling to assist in regeneration of tissue normally found at the site where the matrix is implanted. For example, an acellular tissue matrix, when implanted on or into subdermal tissue, fascia, mammary tissue, or other tissue, may be selected to allow regeneration of the tissue without excessive fibrosis or scar formation. In certain embodiments, the devices can be formed from ALLODERM® or STRATTICE™ (LIFECELL® CORPORATION, BRANCHBURG, N.J.) which are human and porcine acellular dermal matrices, respectively. Alternatively, other suitable acellular tissue matrices can be used. For example, a number of biological scaffold materials as described by Badylak et al., or any other similar materials, can be used to produce tissues with a stable three-dimensional shape. Badylak et al., "Extracellular Matrix as a Biological Scaffold Material: Structure and Function," *Acta Biomaterialia* (2008), doi:10.1016/j.actbio.2008.09.013. The devices described herein can be produced from a variety of different human or animal tissues including human, porcine, ovine, bovine, or other animal tissues.

In some cases, the tissue matrices can be produced from materials that include a basement membrane on at least one surface. For example, the devices can be produced from an acellular dermal matrix, and either the top surface 14 or bottom surface 12 can include an epithelial basement membrane across the surface. During implantation, the device 10 should generally be positioned such that the basement membrane surface is positioned facing the most vascular tissue. For example, as discussed below, when implanted next to a breast implant or tissue expander, the basement membrane covered surface may face towards the implant or tissue expander such that the surface not including a basement membrane faces overlying vascularized tissue.

Figure 5:
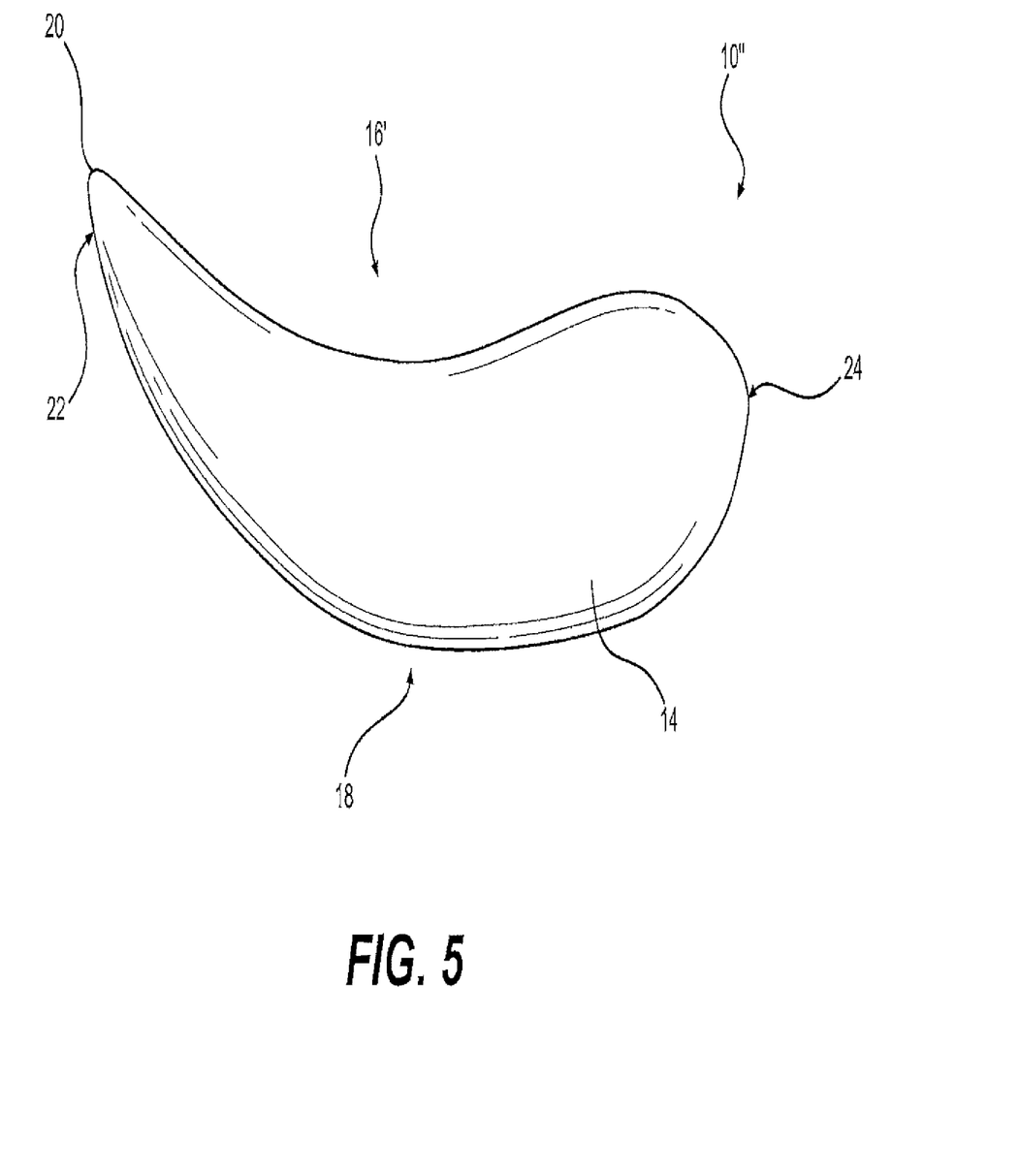
FIG. 5 illustrates a breast treatment device, including a pre-shaped tissue matrix, according to other embodiments.
Figure 6:
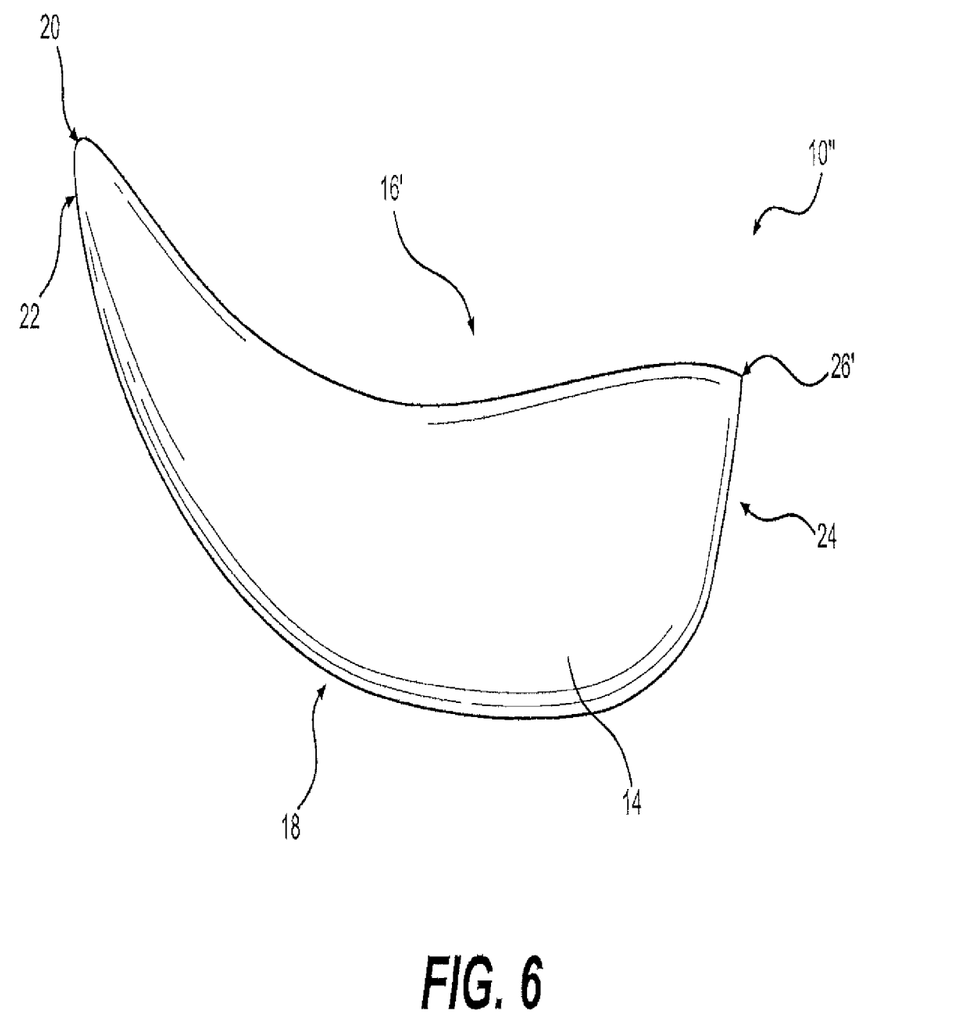
FIG. 6 illustrates a breast treatment device, including a pre-shaped tissue matrix, according to other embodiments.

The devices and systems disclosed herein can also have other shapes and configurations. For example, FIG. 5 illustrates a perspective view of a breast treatment device 10", including a pre-shaped tissue matrix, according to other embodiments. FIG. 6 illustrates a perspective view of a variation of the device 10" shown in FIG. 5.

As shown, the device 10" includes a sheet of acellular tissue matrix. And similar to FIGS. 1, 2, and 4, the sheet of acellular tissue matrix comprises a flexible sheet with a top surface 14 and a bottom surface 12 (not shown but reflected on back side of device 10"). The device 10" also includes a peripheral border, wherein the peripheral border comprises a first edge 16' having a concave shape, and a convex-shaped second edge 18.

Similar to the devices discussed above, the device 10" can include a first end 22 and second end 24, and the first edge 16' and second edge 18 can be joined at the first end 22 and second end 24. In one embodiment, the first end 22 includes a pointed tip 20, and the second end 24 includes a rounded end. In another embodiment, the first end 22 includes a pointed tip 20, and the second end 24 includes a pointed tip 26' (FIG. 6). Furthermore, the devices shown in FIG. 5-6 can be formed of the materials discussed above, with or without a basement membrane.

Figure 7:
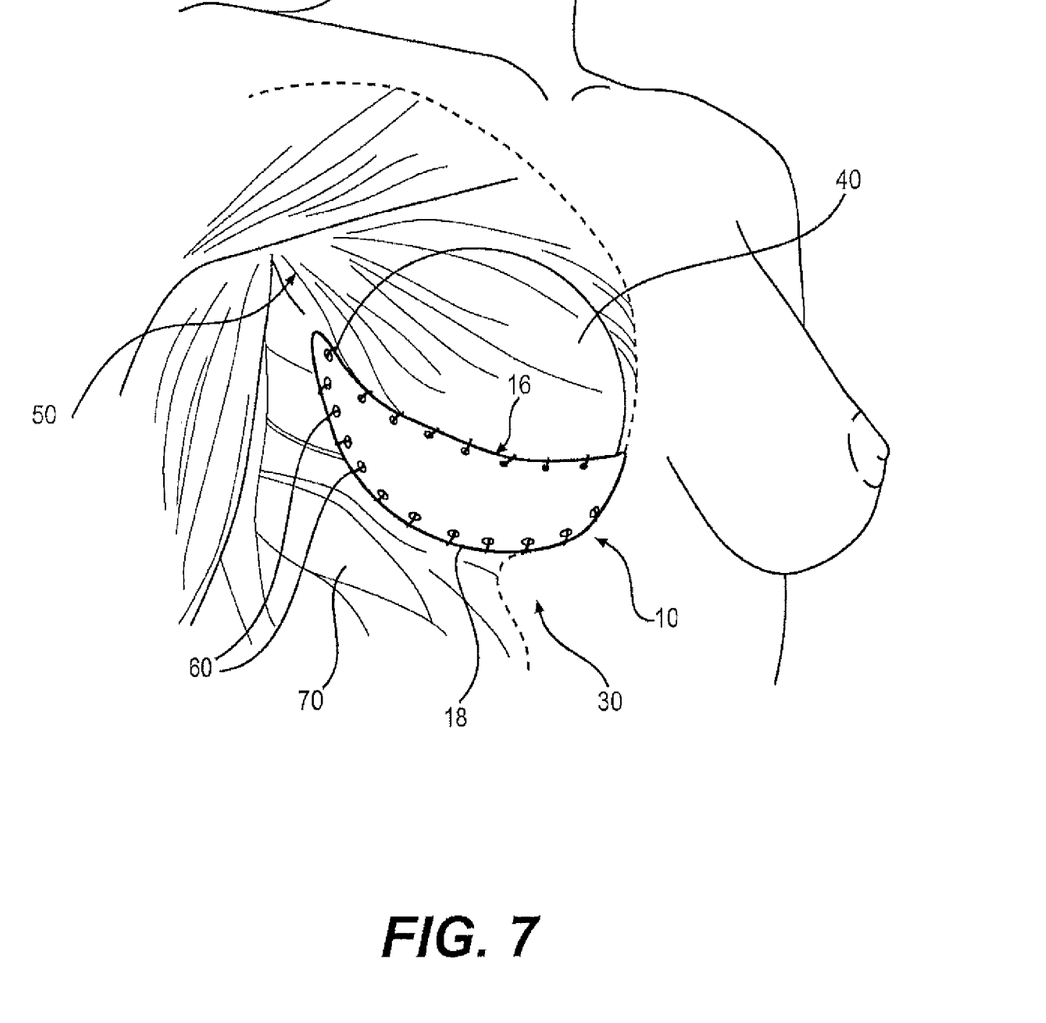
FIG. 7 illustrates implantation of a system for surgical breast procedures, including a pre-shaped tissue matrix implanted along with a breast implant or tissue-expander, according to certain embodiments.

Also disclosed herein are methods for treating a breast. Accordingly, FIG. 3 and FIG. 7 illustrate implantation of a system for surgical breast procedures, including a pre-shaped tissue matrix implanted with a breast implant or tissue-expander, according to certain embodiments. The method can first include identifying an anatomic site within a breast. (As used herein, "within a breast" will be understood to be within mammary tissue, or within or near tissue surrounding the breast such as tissue just below, lateral or medial to the breast, or beneath or within surrounding tissues including, for example, under chest (pectoralis) muscles 50, and will also include implantation in a site in which part or all of the breast has already been removed via a surgical procedure). The site can include, for example, any suitable site needing reconstruction, repair, augmentation, or treatment. Such sites may include sites in which surgical oncology procedures (mastectomy, lumpectomy) have been performed, sites where aesthetic procedures are performed (augmentation or revisions augmentation), or sites needing treatment due to disease or trauma.

After selection of the site, a treatment device is selected. As noted above, various devices including acellular tissue matrices can be used, and the devices can include a flexible sheet having a top surface, a bottom surface, and a peripheral border. The peripheral border and shape of the devices can include any configuration discussed herein.

The method can also include securing at least a portion of the device to a patient. For example, in one embodiment, a portion of the device is secured to a chest wall 70, to surrounding fascia, or to part of an implant or tissue expander 40. In one embodiment, the at least a portion of the second edge 18 is secured to tissue using, for example, suture 60, or other suitable attachments. In addition, other portions of the device 10, including portions of the first edge 16, can be secured to tissue, or if appropriate, to the implant or tissue expander 40 (e.g., via surface features on a tissue expander.)

The methods disclosed herein can also include implantation of an implant or tissue expander 40 under or near part of the device 10, 10', 10". In some cases, no implant or expander will be used, but the device 10, 10', 10" will be implanted to provide added tissue, e.g., for incision closure after mastectomy. In other cases, the implant or expander 40 will be implanted at the same time as the device 10, 10', 10", or in a subsequent surgical procedure.

In addition, FIG. 3 and FIG. 7 illustrate implantation of a device in a right breast, but it will be appreciated that similar devices can be used for treatment of the left breast using a device having a mirror image to that of the devices illustrated in FIG. 3 and FIG. 7. Further, if a basement membrane is included, the basement membrane may similarly be positioned to face a tissue expander or implant, as discussed above.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:

1. A breast treatment device, comprising:
    a sheet of acellular tissue matrix, wherein the sheet of acellular tissue matrix comprises:
        a first end;
        a second end opposite the first end, the first end and the second end being differently shaped;
        a first edge extending from the first end to the second end and consisting of an S-shaped curve having a concave section positioned between a first convex section and a second convex section, and
        a second edge extending from the first end to the second end and consisting of a third convex section;
    wherein the first edge and the second edge meet at the first end and the second end.

2. The device of claim 1, wherein the first end of the device comprises a first pointed tip.

3. The device claim 2, wherein the second end of the device comprises a second pointed tip.

4. The device of claim 1, wherein the second end of the device comprises a rounded edge.

5. The device of claim 1, wherein the tissue matrix comprises a tissue matrix derived from a human tissue.

6. The device of claim 1, wherein the tissue matrix comprises a tissue matrix derived from porcine tissue.

7. The device of claim 1, wherein the tissue matrix comprises a dermal tissue matrix.

8. The device of claim 7, wherein the dermal tissue matrix further comprises an epithelial basement membrane on the top surface of the tissue matrix.

9. A method of treating a breast, comprising:
    identifying an anatomic site within a breast;
    selecting a breast treatment device comprising a sheet of acellular tissue matrix, wherein the sheet of acellular tissue matrix comprises a flexible sheet having a top surface, a bottom surface, a first end, a second end opposite the first end and being differently shaped, and a peripheral border, and wherein the peripheral border comprises a first edge extending from the first end to the second end and consisting of an having a S-shaped curve having a concave section positioned between a first convex section and a second convex section, and an arcuate-shaped second edge extending from the first end to the second end; and
    implanting the treatment device in or proximate the breast; and
    securing at least a portion of the treatment device along the second arcuate-shaped edge to tissue in or near the breast.

10. The method of claim 9, further comprising implanting a breast implant or tissue expander within the breast.

11. The method of claim 10, wherein the breast implant or tissue expander comprises a silicone or saline filled implant or tissue expander.

12. The method of claim 9, wherein the treatment device is implanted with the arcuate-shaped second edge facing inferiorly.

13. The method of claim 9, wherein the tissue matrix comprises a tissue matrix derived from a human tissue.

14. The method of claim 9, wherein the tissue matrix comprises a tissue matrix derived from porcine tissue.

15. The method of claim 9, wherein the tissue matrix comprises a dermal tissue matrix.

16. The method of claim 15, wherein the dermal tissue matrix further comprises an epithelial basement membrane on the top surface of the tissue matrix.

17. The method of claim 15, wherein the treatment device is implanted with the top surface facing towards a chest wall of a patient in which the treatment device is implanted.

18. A breast treatment system, comprising:
    a breast implant or tissue expander; and
    a sheet of acellular tissue matrix, wherein the sheet of acellular tissue matrix comprises a flexible sheet with a top surface, a bottom surface, a first end, a second end opposite the first end, and a peripheral border, and wherein the peripheral border comprises a first edge extending from the first end to the second end and consisting of an S-shaped curve having a concave section positioned between a first convex section and a second convex section, and a second edge extending from the first end to the second end and consisting of a third convex section;
    wherein the first edge and the second edge meet at the first end and the second end, and the first end and the second end are differently shaped.

19. The breast treatment system of claim 18, wherein the first end of the sheet of acellular tissue matrix comprises a first pointed tip.

20. The breast treatment system claim 19, wherein the second end of the sheet of acellular tissue matrix comprises a second pointed tip.

21. The breast treatment system of claim 18, wherein the second end of the sheet of acellular tissue matrix comprises a rounded edge.

22. The breast treatment system of claim 18, wherein the tissue matrix comprises a tissue matrix derived from a human tissue.

23. The breast treatment system of claim 18, wherein the tissue matrix comprises a tissue matrix derived from porcine tissue.

24. The breast treatment system of claim 18, wherein the tissue matrix comprises a dermal tissue matrix.

25. The breast treatment system of claim 24, wherein the dermal tissue matrix further comprises an epithelial basement membrane on the top surface of the tissue matrix.

26. A breast treatment device, comprising:
    a sheet of acellular tissue matrix, wherein the sheet of acellular tissue matrix comprises a flexible sheet with a top surface, a bottom surface, a first end, a second end opposite the first end and being differently shaped, and a peripheral border, and wherein the peripheral border consists of a first edge and a second edge that meet at the first end of the device and at the second end of the device;
    wherein the first edge extends from the first end to the second end and consists of an S-shaped curve having a concave section positioned between a first convex section and a second convex section;
    wherein the first end of the device comprises a pointed tip, and the second end of the device comprises a rounded edge, the pointed tip and the rounded edge being differently shaped.

27. The device of claim 26, wherein the tissue matrix comprises a tissue matrix derived from a human tissue.

28. The device of claim 26, wherein the tissue matrix comprises a tissue matrix derived from porcine tissue.

29. The device of claim 26, wherein the tissue matrix comprises a dermal tissue matrix.

30. The device of claim 29, wherein the dermal tissue matrix further comprises an epithelial basement membrane on the top surface of the tissue matrix.

\* \* \* \* \*